United States Patent
Bonnassieux

(10) Patent No.: US 6,520,184 B2
(45) Date of Patent: Feb. 18, 2003

(54) METHOD OF CONTINUOUSLY MANUFACTURING COMPRESSES OR DRAPES FOR SINGLE USE, AND A COMPRESS OR DRAPE OBTAINED BY THE METHOD

(75) Inventor: Gilles Bonnassieux, Pollionnay (FR)

(73) Assignee: Laboratoire Hydrex, Amplepius (FR)

( * ) Notice: Subject to any disclaimer, the term of this patent is extended or adjusted under 35 U.S.C. 154(b) by 0 days.

(21) Appl. No.: 09/028,295

(22) Filed: Feb. 24, 1998

(65) Prior Publication Data

US 2002/0096179 A1 Jul. 25, 2002

(30) Foreign Application Priority Data

Oct. 17, 1997 (FR) .............................. 97 13018

(51) Int. Cl.⁷ ................................. A61F 13/00
(52) U.S. Cl. ......................... 128/849; 28/117
(58) Field of Search ................. 602/41, 44; 128/847, 128/204.18, 910, 140, 849–856; 28/138, 117, 134

(56) References Cited

U.S. PATENT DOCUMENTS

| | | | |
|---|---|---|---|
| 3,809,077 A | * 5/1974 | Hansen | 128/849 |
| 4,157,719 A | 6/1979 | DeWoskin | |
| 5,586,563 A | * 12/1996 | Newman | 128/849 |
| 5,725,517 A | * 3/1998 | DeBusk | 604/362 |
| 5,743,273 A | * 4/1998 | Newman | 128/849 |
| 5,792,128 A | * 8/1998 | DeBusk | 604/362 |

FOREIGN PATENT DOCUMENTS

| | | |
|---|---|---|
| EP | 0/267861 | 5/1988 |
| EP | 0702938 | 3/1996 |
| GB | 716923 | 10/1954 |

* cited by examiner

*Primary Examiner*—Dennis Ruhl
(74) *Attorney, Agent, or Firm*—Horst M. Kasper

(57) ABSTRACT

The invention relates to a compress or drape for single use, constituted by a plurality of alternating superposed sheets of hydrophilic cotton gauze and of non-woven hydrophilic web, and to a method of manufacturing it, the method comprising the following steps: making a continuous multilayer strip by simultaneously paying out sheets of hydrophilic cotton gauze and of non-woven web from reels, said sheets passing together via a drive device before reaching stations for making up individual drapes; putting non-woven bands around the longitudinal edges of the multilayer strip by paying out from payout spools; assembling the bands in a bonding station by means of ultrasonic bond lines; cutting individual drapes to length transversely in a cutting station; taking off the cut-apart drapes perpendicularly in a drive device; and putting bands into place around the transverse edges of the individualized drapes, and securing them by ultrasonic bonding.

25 Claims, 3 Drawing Sheets

METHOD OF CONTINUOUSLY MANUFACTURING COMPRESSES OR DRAPES FOR SINGLE USE, AND A COMPRESS OR DRAPE OBTAINED BY THE METHOD

The present invention relates to a method of continuously manufacturing compresses or drapes for single use, constituted by a plurality of superposed alternating layers of hydrophilic cotton gauze and of non-woven hydrophilic web, the outer layers being of hydrophilic cotton gauze. The invention also relates to a compress or drape obtained by the method.

BACKGROUND OF THE INVENTION

Single use drapes of this type are used in particular in hospitals for surgical purposes, e.g. as a wall drape covering the edges of a wound after incision and before spreaders have been put into place. They can also be used as abdominal drapes on which viscera or intestinal loops can be laid out. If previously moistened, they can be used to protect an organ that is sensitive to drying out.

Drapes are known that are made of cotton, of polyester with cotton, or of polyester with microfiber, and which are washed and disinfected after each use, and then refolded, reconditioned, and resterilized, thus giving rise to a danger of accidental contamination in laundries during the handling of soiled drapes. Such drapes also suffer from the drawback of shedding particles of cotton fluff which can give rise to infections.

To mitigate those drawbacks, inherent to known drapes for multiple uses after reconditioning, French patent No. 2 724 838 and European patent application 0 702 9.38 A1 in the name of the Applicant propose a drape for single use made up a plurality of superposed alternating sheets of hydrophilic cotton gauze and of non-woven web. That drape is manufactured by means of a method that essentially comprises the following steps: on a single continuous sheet of hydrophilic cotton gauze there are placed two non-woven sheets each of width corresponding to one-third the width of the hydrophilic cotton gauze sheet so as to leave one-third of its width unoccupied; the multilayer strip is obtained by folding so that the hydrophilic cotton gauze forms the outer layers of the multilayer strip.

Unlike known products that are somewhat similar thereto, that drape, which is manufactured without using adhesive for assembling the various layers together, has the advantage of bringing the wound into contact with natural fiber that does not become shaggy, combined with the absorption capacity of a non-woven fiber as constituted, for example, by absorbent viscose and polypropylene, a polyester compound and viscose, a polyester, or a polyamide.

By associating differing materials, namely a woven material and a non-woven material, it is possible to combine the respective advantages of both of them: the woven material has strength that remains unchanged whether it is dry or wet, whereas a non-woven material is weaker when wet. In addition, the hydrophilic cotton gauze provides a "cloth feel" and its high strength in tension ensures that the finished product is strong. In contrast, the non-woven material has very high absorption capacity. Drapes of that type possess absorption capacity that is twice as large a conventional drape of woven material while still being very strong.

That type of material has been developed by the Applicant and gives complete satisfaction in use. However, to comply with economic imperatives, it is desirable to seek to simplify the method of manufacturing drapes of that type as proposed by the Applicant in the above-mentioned patent documents, in order to reduce the cost of manufacturing the product and make it more competitive.

OBJECTS AND SUMMARY OF THE INVENTION

Consequently, an object of the present invention is to provide a method of continuously manufacturing compresses and drapes of the above-described type associating two different materials, namely the hydrophilic cotton gauze and the non-woven web, which method is simpler to implement and makes it possible to reduce the cost of manufacturing the product.

To achieve those objects, the present invention proposes a method of continuous manufacture which comprises the following steps:

a single continuous multilayer strip or sheet is made by simultaneously paying out sheets or strips of hydrophilic cotton gauze and of non-woven web from payout spools or reels, which may be associated with at least one device for automatically adjusting the tension of the strips, said strips passing together via a motorized drive device prior to reaching stations for making up individual drapes;

continuous non-woven ribbons or bands are put into place on the longitudinal edges of the multilayer strip by being paid out from spools, said bands being folded around the longitudinal edges of the multilayer strip over the outer sheets to form a hems;

the ribbons or bands folded around the longitudinal edges of the multilayer strip are assembled in a bonding station by means of ultrasonic bonds passing through the folded-over branches of the band and through all of the layers of the multilayer strip;

individual drapes are cut transversely to length in a cutting station and optionally dust is sucked up by means of a suction device;

the cut of drape is taken up perpendicularly by a drive device; and hem-forming ribbons or bands are placed around the transverse edges of the individualized drapes and are secured to said folded-over ribbons or bands by ultrasonic bonding.

In a preferred implementation of the invention, the sheets constituting the multilayer strip are assembled together and the ribbons or bands folded around the four edges of the drapes to form hems are fixed in place by ultrasonic bonding. Nevertheless, it is also possible to replace ultrasonic bonding by a stitching technique.

In order to ensure that the strips constituting the multilayer strip are properly paid out, it is advantageous, in accordance with the invention, to provide for the tension of the strips of hydrophilic cotton gauze to be obtained by traction exerted on said strips by a drive device and by braking the payout spools or reels, whereas the tension of the non-woven strip can be obtained after motor-driven payout from the corresponding spool or reel by means of a device for automatically adjusting the tension of said strip, which device is placed between the payout spool and the drive device, and because of the non-woven strip being driven by friction between the strips of hydrophilic cotton gauze, themselves driven by the drive device. It is also possible to provide a device for automatically adjusting the tension of the multilayer strip, which device is interposed between firstly the station for putting the longitudinal ribbons or bands into place and/or the bonding station, and secondly the station for cutting out the individual drapes.

According to another characteristic of the invention, it is advantageous to include an X-ray detectable thread in at least one of the hems of the drapes. To this end, a thread, e.g. of barium sulfate impregnated polyester, is placed along at least one of the longitudinal edges of the multilayer strip prior to or simultaneously with the ribbons or bands being put into place and being secured by ultrasonic bonding or by stitching. Naturally, it is also possible to integrate an X-ray detectable thread in analogous manner in at least one of the transverse hems of a drape.

In order to hold the drapes or the sheets making up the multilayer strip in place in a single unit and in order to prevent them from separating from one another and thus running the risk of damaging the drape, it is advantageous to make provision for a plurality of longitudinal lines of ultrasonic bonding or stitching to be applied, which lines should be distributed at uniform intervals over the entire width of the multilayer strip or of the drape, preferably before the band is put into place along the longitudinal edges thereof, and in any event before the strip is cut up into individual drapes.

The compress or drape for single use manufactured by the method of the invention is made up of a plurality of layers, preferably three layers, comprising, in alternation, hydrophilic cotton gauze and non-woven hydrophilic web, with the outer layers being of hydrophilic cotton gauze; the drape has its edges finished by ribbons or bands of non-woven web forming hems, secured to the component sheets by ultrasonic bonding or by stitching, and an X-ray detectable thread is included in at least one of the four hems, and in addition longitudinal lines of ultrasonic bonding or of stitching are provided that are spaced apart from one another and that are distributed over the entire width of the drape.

BRIEF DESCRIPTION OF THE DRAWINGS

The invention is explained purely by way of indication with reference to the accompanying drawings given as non-limiting examples.

MORE DETAILED DESCRIPTION

A reference key for the various references used in the description is to be found at the end of the description.

Figure 1A:
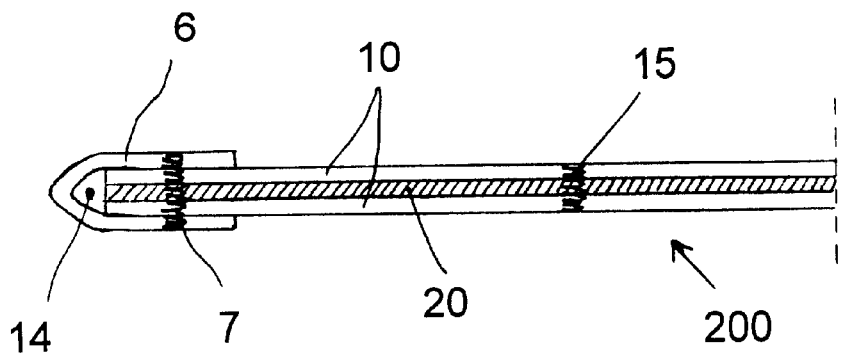
FIG. 1A is a fragmentary section through a three-layer drape made by the method of the invention.
Figure 1B:
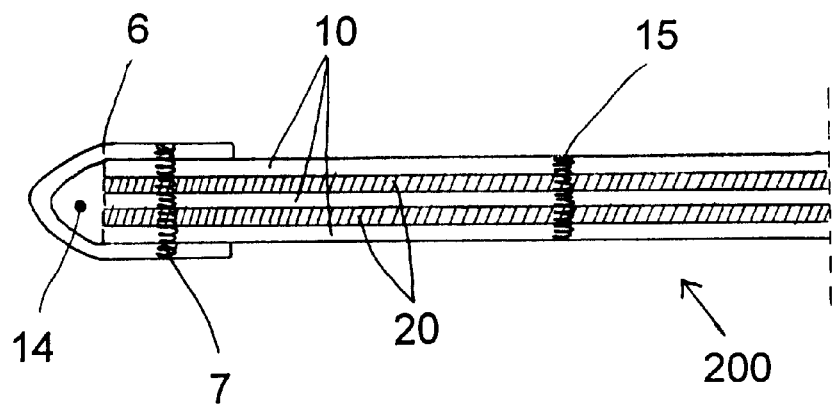
FIG. 1B is a fragmentary section through a five-layer drape made by the method of the invention.
Figure 2:
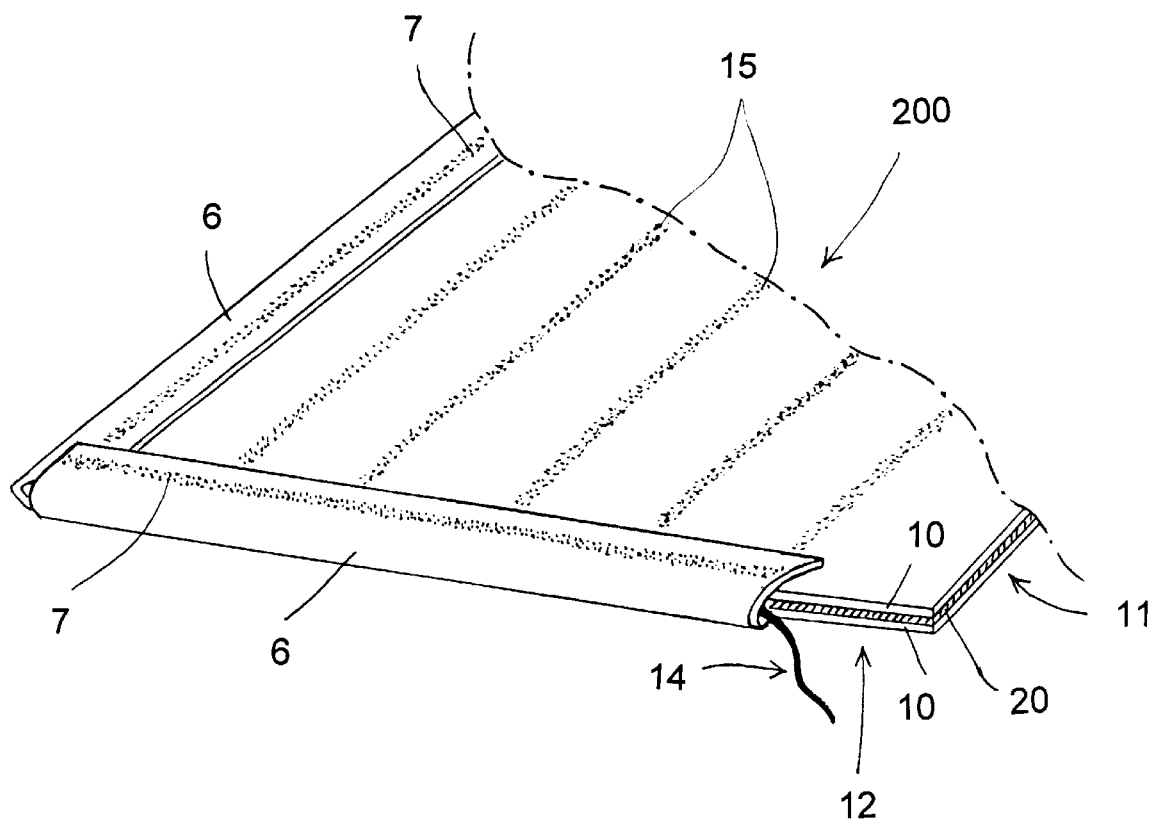
FIG. 2 is a partially cutaway fragmentary perspective view of a drape made by the method of the invention.

FIGS. 1A and 1B are fragmentary sections through two variant embodiments of a single-use drape (200) in accordance with and manufactured by the method of the invention. FIG. 2 is a partially cutaway fragmentary perspective view of the drape shown in FIG. 1A.

The drape (200) in FIGS. 1A and 2 comprises two outer sheets (10) of hydrophilic cotton gauze with an inner sheet (20) of non-woven web material disposed therebetween. In the context of the invention, and as shown in FIG. 1B, the multilayer drape may equally well have five or more superposed sheets, so long as the outer sheets are always made of hydrophilic cotton gauze. As is conventional in surgery, the hydrophilic cotton gauze sheets are preferably green or blue in color so as to avoid dazzle.

The multilayer strip from which individual drapes (200) are made is of a width that is adapted to the intended use, generally lying in the range 40 cm to 100 cm. The hydrophilic cotton gauze (10) has a gauge that varies as a function of the intended use of the drape and its looked-for degree of absorption, said gauge preferably lying in the range 13 threads/cm$^2$ to 20 threads/cm$^2$. In general, the weight of the cotton gauze will lie in the range 30 grams per square meter (g/m$^2$) to 100 g/m$^2$.

The intermediate sheet (20) is constituted by a non-woven material that is adapted to be absorbent to the looked-for degree. It may advantageously be constituted by absorbent viscose with polypropylene, polyester with viscose, polyester, or polyamide.

The association of these two materials used respectively for the layers (10) and for the layer (20) makes it possible to combine the advantages inherent to each of them, and in particular the strength and the "cloth feel" of the cotton gauze, and the high power of absorption of the non-woven web.

The four edges of drapes (200) as shown in FIGS. 1A, 1B, and 2 are finished by means of a ribbon or band (6) of non-woven material, folded over the outer sheets (10) and forming a hem, being held in place by ultrasonic bonding (7) passing through all of the thicknesses, i.e. through the folded-over branches of the band (6) and through the sheets (10) and (20). The sheets of the drape (200) are provided with longitudinal ultrasonic bonding (15) distributed across its entire width, and spaced apart from one another at a pitch of 5 cm to 8 cm, for example, thereby contributing to holding together the component layers of the drape and preventing them from separating from one another which could damage the drape.

In accordance with the invention, it is advantageous to provide for an X-ray detectable thread (14) to be integrated in at least one of the four hems of the drape (200). For example, this can be a polyester thread impregnated with barium sulfate. The X-ray detectable thread fed from a corresponding reel or payout means is advantageously put into place before or simultaneously with the ribbon or band (6) being put into place on the longitudinal edges (11) of the multilayer strip (100). It is also possible and in analogous manner to integrate an X-ray detectable thread in the hem of the second longitudinal edge (11) and/or in at least one of the transverse edge hems (12).

The ribbon or band (6) of non-woven material and folded over the outside faces of the drape covers the longitudinal edges (11) and the transverse edges (12) thereof closely, but it is acceptable for the band (6) to project by up to about 5 mm beyond the edges of the drape.

Figure 3:
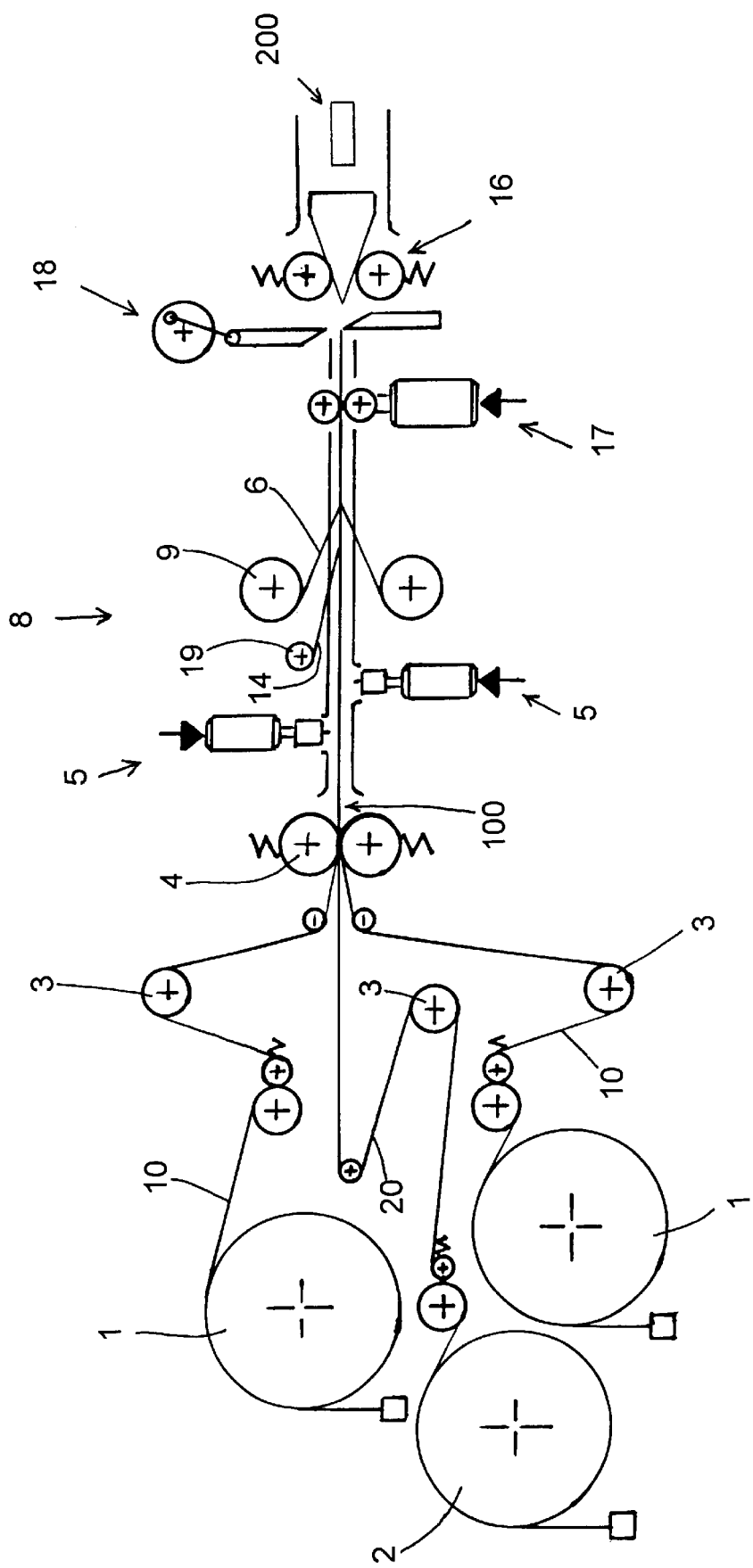
FIG. 3 is a diagrammatic side view of a machine used for implementing the manufacturing method of the invention.

The single-use drape is manufactured by the continuous method proposed by the invention. This method is illustrated by way of example by the diagram of a machine shown in FIG. 3, and it takes place in application of the following steps:

making a single continuous multilayer sheet or strip (100) by simultaneously paying out sheets or strips of hydrophilic cotton gauze (10) and a non-woven web (20) from payout spools (1, 2) which may be associated with at least one device (3) for automatically regulating tension in the strips, said strips (10, 20) passing together via a motorized drive device (4) before reaching stations (5, 8, 17, 18) for making up individual drapes (200);

paying out continuous non-woven ribbons or bands (6) from payout spools (9) onto the longitudinal edges (11)

of the multilayer strip (100), said bands being folded around the longitudinal edges of the multilayer strip over the outer sheets of hydrophilic cotton gauze (10) to form a hem, this operation being performed in a station (8) for putting into place the ribbons or bands;

assembling the ribbons or bands (6) folded around the longitudinal edges (11) of the multilayer strip (100) in a bonding station (17) operating by ultrasonic bonds (7) passing through the folded-over branches of the bands and through all of the layers of the multilayer strip (100);

cutting individual drapes (200) transversely to length in a cutting station (18) and optionally sucking up dust by means of a suction device;

taking the cut drape (200) perpendicularly by means of a drive device (16); and placing hem-forming ribbons or bands (6) around the transverse edges (12) of the cut drape, said folded-over ribbons or bands being secured by ultrasonic bonding (7).

Still in accordance with the invention, it can be advantageous to apply a plurality of longitudinal lines of ultrasonic bonding (15) distributed at regular intervals across the entire width of the multilayer strip prior to cutting the strip up into individual drapes (200), these lines of bonding being preferably implemented in a bonding station (5) disposed upstream from the station (8) for putting the ribbons or bands (6) into place.

In a preferred embodiment, provision is made to place an X-ray detectable thread (14), e.g. a polyester thread impregnated with barium sulfate, along at least one of the longitudinal edges of the multilayer strip (100). This X-ray detectable thread (14) is advantageously placed along at least one of the longitudinal edges of the multilayer strip (100). The X-ray detectable thread (14) is preferably put into place before or simultaneously with the ribbon or band (6) being put into place. To this end, the reel or payout spool (19) for the X-ray detectable thread (14) is advantageously located immediately upstream from the spool (9) for paying out the band (6) so as to integrate the X-ray detectable thread (14) in the corresponding hem. Proper paying out of the X-ray detectable thread (14) and of the ribbons or bands (6) can be ensured by a device for automatically regulating tension.

In order to ensure that the strips (19, 20) making up the multilayer strip (100) constituting the individual drapes are paid out properly, it is advantageous, in accordance with the invention, to provide for the tension of the hydrophilic cotton gauze strips to be obtained by traction exerted on said strips by a drive device (4) and by braking the corresponding reels or spools (1), while the tension of the non-woven web (20) is obtained, after motorized paying out from the corresponding spool or reel (2), by means of a device (3) for automatically adjusting the tension of said strip (100) and disposed between the spool (2) and the drive device (4), and because of drive by friction against said non-woven strip (2) between the strips of hydrophilic cotton gauze (10), themselves driven by the drive device (4). Provision may also be made for a device that automatically adjusts the tension of the multilayer strip, which device may be interposed, for example, between the station (8) for putting the longitudinal ribbons or bands into place and/or the bonding station (17), and the station (18) for cutting up the individual drapes (200).

In a preferred embodiment of the invention, the sheets (10, 20) making up the multilayer strip (100) are assembled together and the ribbons or bands (6) folded around the four sides of the drapes to form hems are fixed by means of ultrasonic bonding (7). However, it is also possible to replace ultrasonic bonding by assembly by means of stitching. Thus, the longitudinal ultrasonic bonds (15) distributed across the entire width of the drape and the ultrasonic bonds (7) for assembling the bands (6) overlying the edges of the finished product can be replaced by lines of stitching performed in stitching stations in a manner analogous to and during corresponding steps of the above-explained manufacturing method.

Reference Key

1 Reel or spool for paying out the strip of hydrophilic cotton gauze.
2 Reel or spool for paying out the strip of non-woven web.
3 Device for automatically adjusting tension.
4 Drive device.
5 Station for bonding by means of longitudinal bond lines (15).
6 Ribbon or band of non-woven material.
7 Ultrasonic bonds for assembling the bands (6).
8 Station for putting the bands (6) into place.
9 Reel or spool for paying out band (6).
10 Strip or sheet of hydrophilic cotton gauze.
11 longitudinal edges of the multilayer strip (100).
12 Transverse edges of the multilayer strip (100).
14 X-ray detectable thread.
15 Longitudinal lines of ultrasonic bonding.
16 Drive device.
17 Bonding station.
18 Station for cutting individual drapes apart.
19 Reel or spool for paying out the X-ray detectable thread (14).
20 Strip or sheet of non-woven material.
100 Continuous multilayer strip.
200 Individual drape or compress.

What is claimed is:

1. A method of continuously manufacturing compresses or drapes for single use, the method comprising the following steps:

a single continuous multilayer strip is made by simultaneously delivering sheets or strips of hydrophilic cotton gauze and of non-woven web from supply spools or reels, which are connected to a device for automatically adjusting the tension of the sheets or strips of hydrophilic cotton gauze and of non-woven web, said sheets or strips of hydrophilic cotton gauze and of non-woven web running together to form a multilayer strip via a motorized drive device prior to reaching stations for making up individual drapes, wherein outer sheets consist of hydrophilic cotton gauze;

continuous non-woven ribbons or bands are put into place on longitudinal edges of the multilayer strip by being delivered from spools, said continuous non-woven ribbons or bands being folded around the longitudinal edges of the multilayer strip over the outer sheets to form hems;

the continuous non-woven ribbons or bands folded around the longitudinal edges of the multilayer strip are assembled in a bonding station by means of ultrasonic bonds passing through folded-over branches of the continuous non-woven ribbons or bands and through all of the layers of the multilayer strip;

individual drapes are cut transversely to length in a cutting station and dust is sucked up by means of a suction device;

the cut of the drapes is taken up perpendicularly by a drive device; and hem-forming ribbons or bands are placed around transverse edges of individualized drapes and are secured to folded-over hem-forming ribbons or bands by ultrasonic bonding, wherein the compresses or drapes are constituted by a plurality of superposed alternating sheets of hydrophilic cotton gauze and of non-woven web, the outer sheet being of hydrophilic cotton gauze, and wherein the transverse edges are finished by means of respective non-woven hem-forming ribbons or bands that form hems, secured by ultrasonic bonding or by stitching, an X-ray detectable thread being integrated in at least one of the hems.

2. A method according to claim 1, wherein a plurality of longitudinal lines of ultrasonic bonding are applied that are distributed at regular intervals over the entire width of the multilayer strip prior to the strip being cut up into individual drapes and preferably prior to the bands being placed around its longitudinal edges.

3. A method according to claim 1, wherein the device for automatically adjusting the tension of the multilayer strip is used, which device is interposed between the station for putting the longitudinal ribbons or bands into place and/or the bonding station and the station for cutting out the individual drapes.

4. A method according to claim 1, wherein an X-ray detectable thread furnished by a thread of polyester impregnated with barium sulfate is put into place along at least one of longitudinal edges of the multilayer strip before or simultaneously with the hem-forming ribbons or bands being put into place, so as to integrate said X-ray detectable thread in the hem(s).

5. A method according to claim 1, wherein an X-ray detectable thread furnished as a polyester thread impregnated with barium sulfate is integrated in at least one of the hems around transverse edges of individualized drapes.

6. A method of continuously manufacturing compresses or drapes for single use, the method comprising the following steps:

a single continuous multi-layer strip is made by simultaneously delivering sheets or strips of hydrophilic cotton gauze and of non-woven web including outer sheets from supply spools or reels, which are connected to a device for automatically adjusting the tension of the sheets or strips of hydrophilic cotton gauze and of non-woven web, said sheets or strips of hydrophilic cotton gauze and of non-woven web running together to form a multi-layer strip via a motorized drive device prior to reaching stations for making up individual drapes, wherein the outer sheets consist of hydrophilic cotton gauze;

continuous non-woven ribbons or bands are put into place on longitudinal edges of the multi-layer strip by being delivered from spools, said continuous non-woven ribbons or bands being folded around the longitudinal edges of the multi-layer strip over the outer sheets to form hems;

the continuous non-woven ribbons or bands folded around the longitudinal edges of the multi-layer strip are assembled in a stitching station by means of stitching passing through folded-over branches of the continuous non-woven ribbons or bands and through all of the layers of the multi-layer strip;

individual drapes are cut transversely to length in a cutting station and dust is sucked up by means of a suction device;

the cut of drapes is taken up perpendicularly by a drive device; and hem-forming ribbons or bands are placed around the transverse edges of individualized drapes and are secured by stitching.

7. A method according to claim 3, wherein a plurality of longitudinal lines of stitching are applied that are distributed at regular intervals over the entire width of the multilayer strip prior to the strip being cut up into individual drapes, and preferably prior to the bands being placed around the longitudinal edges.

8. A method according to claim 2 or 7, wherein the tension of the sheets or strips of hydrophilic cotton gauze and of non-woven web is obtained by traction exerted on said strips by the motorized drive device and by braking the supply spools or reels, and wherein the tension of the sheets or strips of hydrophilic cotton gauze and of non-woven web is obtained after motor-driven delivery from the spool or reel by means of the motorized drive device for automatically adjusting the tension of said sheets or strips of hydrophilic cotton gauze and of non-woven web, which motorized drive device is placed between the payout spool and the drive device, and because of the sheets or strips of hydrophilic cotton gauze and of non-woven web being driven by friction between the sheets or strips of hydrophilic cotton gauze and of non-woven web, themselves driven by the motorized drive device.

9. A method of continuously manufacturing compresses or drapes for single use comprising the following steps:

connecting reels to a device for automatically adjusting the tension of strips of hydrophilic cotton gauze and of non-woven hydrophilic web;

simultaneously delivering strips of hydrophilic cotton gauze and of non-woven hydrophilic web from supply reels;

running said strips of hydrophilic cotton gauze and of non-woven hydrophilic web together through a motorized drive device;

making up individual compresses or drapes in stations after running said strips together to form a multilayer strip;

delivering continuous non-woven ribbons or bands from spools;

putting the continuous non-woven ribbons or bands into place on longitudinal edges of the multilayer strip, wherein the multilayer strip is constituted of a plurality of superposed alternating sheets of said hydrophilic cotton gauze and of non-woven hydrophilic web, with outer sheets of said multilayer strip being of hydrophilic cotton gauze;

folding the continuous non-woven ribbons or bands around the longitudinal edges of the multilayer strip and over said outer sheets to form first hems;

assembling the continuous non-woven ribbons or bands that are folded around the longitudinal edges of the multilayer strip in a bonding station;

generating ultrasonic bonds through said first hems and through all layers of the multilayer strip;

cutting individual compresses or drapes transversely to length in a cutting station;

sucking up dust with a suction device;

taking up the transversely cut compresses or drapes perpendicularly by a drive device; and placing hem-forming second ribbons or bands forming second hems around transverse edges of individualized compresses or drapes;

securing the transverse edges of individualized compresses or drapes to the hem-forming second ribbons or bands by ultrasonic bonding;

finishing the transverse edges by means of said second ribbons or bands that form second hems;

integrating an x-ray detectable thread in at least one of the hems.

10. A method of continuously manufacturing compresses or drapes for single use comprising the following steps:

connecting supply reels to a device for automatically adjusting the tension of strips of hydrophilic cotton gauze and of non-woven hydrophilic web;

simultaneously delivering strips of hydrophilic cotton gauze and of non-woven hydrophilic web from the supply reels;

running said strips of hydrophilic cotton gauze and of non-woven hydrophilic web together through a motorized drive device for forming a multilayer strip constituted of a plurality of superposed alternating strips of said hydrophilic cotton gauze and of non-woven hydrophilic web, with outer strips of said multilayer strip being of hydrophilic cotton gauze;

delivering continuous non-woven ribbons or bands from spools;

placing the continuous non-woven ribbons or bands on longitudinal edges of the multilayer strip;

folding the continuous non-woven ribbons or bands around the longitudinal edges of the multilayer strip and over said outer strips to form first hems;

assembling the continuous non-woven ribbons or bands that are folded around the longitudinal edges of the multilayer strip in a bonding station;

generating ultrasonic bonds through said first hems and through all layers of the multilayer strip;

cutting the multilayer strip transversely to a longitudinal direction in a cutting station to separate individual compresses or drapes, wherein individual compresses or drapes are made up in stations from the multilayer strip;

taking up the transversely cut compresses or drapes in a direction perpendicular to the longitudinal direction of the multilayer strip by a drive device; and placing hem-forming second ribbons or bands forming second hems around transverse edges of individualized compresses or drapes;

attaching the transverse edges of individualized compresses or drapes to the hem-forming second ribbons or bands by ultrasonic bonding;

finishing the transverse edges by means of said second ribbons or bands that form second hems;

integrating an X-ray detectable thread in at least one of the hems.

11. The method according to claim 10 further comprising producing the hem-forming second ribbons or bands of a non-woven material;

delivering hem-forming second ribbons or bands from second spools;

folding the hem-forming second ribbons or bands around the transverse edges of the individualized compresses or drapes to form the second hems.

12. The method according to claim 10 further comprising forming a plurality of longitudinal lines of ultrasonic bonding distributed at regular intervals over the entire width of the multilayer strip prior to the strip being cut up into individual compresses or drapes; and placing thereafter the continuous non-woven ribbons or bands around the longitudinal edges of the multilayer strip.

13. The method according to claim 10 further comprising placing the motorized drive device between the supply reels and the drive device;

exerting traction on said strips of hydrophilic cotton gauze and of non-woven web by the motorized drive device and by braking the supply reels for obtaining a tension of the strips of hydrophilic cotton gauze and of non-woven web;

obtaining the tension of the strips of hydrophilic cotton gauze and of non-woven web after motor-driven delivery from the supply reels by means of the motorized drive device for automatically adjusting the tension of said strips of hydrophilic cotton gauze and of non-woven web;

depositing the strips of hydrophilic cotton gauze and of non-woven web by friction between the strips of hydrophilic cotton gauze and of non-woven web, wherein the strips of hydrophilic cotton gauze and of non-woven web themselves are driven by the motorized drive device.

14. The method according to claim 10 further comprising interposing a device for automatically adjusting the tension of the multi-layer strip between a station for putting the longitudinal ribbons or bands into place and/or the bonding station;

employing the device for automatically adjusting the tension of the multi-layer strip.

15. The method according to claim 10 further comprising furnishing the X-ray detectable thread by a thread of polyester impregnated with barium sulfate;

putting the X-ray detectable thread into place along at least one of longitudinal edges of the multilayer strip before or simultaneously with the hem-forming ribbons or bands being put into place for integrating said X-ray detectable thread in the first hems.

16. The method according to claim 10 further comprising furnishing the X-ray detectable thread by a polyester thread impregnated with barium sulfate;

integrating in the X-ray detectable thread at least one of the second hems around transverse edges of individualized compresses or drapes.

17. A method of continuously manufacturing drapes for single use, the method comprising the following steps:

simultaneously delivering strips of hydrophilic cotton gauze from first supply spools and a non-woven strip from a second supply spool for making a single continuous multi-layer strip;

connecting the strips of hydrophilic cotton gauze to a first device for automatically adjusting the tension of the strips of hydrophilic cotton gauze;

connecting the non-woven strip to a second device for automatically adjusting the tension of the non-woven strip;

running together the strips of hydrophilic cotton gauze and of non-woven strip to form the multi-layer strip with a first motorized drive device prior to reaching stations for making up individual drapes, wherein two of the strips of hydrophilic cotton gauze are disposed on outer sides of the multi-layer strip;

continuous non-woven longitudinal bands are put into place on longitudinal edges of the multi-layer strip by being delivered from third supply spools, said continuous non-woven longitudinal bands being folded around the longitudinal edges of the multi-layer strip over the two of the strips of hydrophilic cotton gauze disposed on outer sides of the multi-layer strip to form hems of drapes;

assembling the continuous non-woven longitudinal bands folded around the longitudinal edges of the multi-layer strip in a bonding station by means of ultrasonic bonds passing through folded-over branches of the continuous non-woven longitudinal bands and through the multi-layer strip to form longitudinal hems;

cutting drapes transversely to length in a cutting station to form individual transversely cut drapes having transverse edges;

sucking up dust by means of a suction device;

taking up the transversely cut drapes in a perpendicular direction with a second motorized drive device; and placing non-woven hem-forming transverse ribbons around the transverse edges of transversely cut drapes;

securing said folded-over hem-forming transverse ribbons to the transverse edges of the transversely cut drapes by ultrasonic bonding to form transverse hems, wherein the transversely cut drapes are constituted by a plurality of superposed alternating strips of hydrophilic cotton gauze and of a non-woven strips, wherein two strips of hydrophilic cotton gauze are disposed on respective outer sides of the transversely cut drapes;

integrating an X-ray detectable thread in at least one of the longitudinal hems and transverse hems.

18. A method of continuously manufacturing compresses for single use, the method comprising the following steps:

delivering a first strip of hydrophilic cotton gauze from a first gauze supply spool;

delivering a first non-woven strip from a first non-woven strip supply spool simultaneously with the first strip of hydrophilic cotton gauze;

delivering a last strip of hydrophilic cotton gauze from a last gauze supply spool simultaneously with the first strip of hydrophilic cotton gauze;

sequentially superposing and transporting the first strip of hydrophilic cotton gauze, the first non-woven strip and the last strip of hydrophilic cotton gauze in a first motorized drive device and thereby obtaining a single continuous multilayer strip having a first longitudinal edge and having a second longitudinal edge;

folding a first continuous non-woven longitudinal band around the first longitudinal edge;

folding a second continuous non-woven longitudinal band around the second longitudinal edge;

assembling the first continuous non-woven longitudinal band around the first longitudinal edge in a bonding station by means of ultrasonic bonds passing through to form a first hem;

assembling the second continuous non-woven longitudinal band around the second longitudinal edge in the bonding station by means of ultrasonic bonds passing through to form a second hem and thereby a multilayer strip with longitudinally attached hems;

cutting the multilayer strip with longitudinally attached hems to a predefined length in a cutting station with a cut disposed perpendicular to a longitudinal direction to form individual transversely cut pre-compresses having a leading transverse edge and having a trailing transverse edge;

taking up the transversely cut pre-compresses in a perpendicular direction with a second motorized drive device;

folding a leading hem-forming transverse ribbon around the leading transverse edge of transversely cut pre-compresses;

folding a trailing hem-forming transverse ribbon around the trailing transverse edge of transversely cut pre-compresses;

assembling the leading hem-forming transverse ribbon around the leading transverse edge of transversely cut pre-compresses by ultrasonic bonding to form a leading transverse hem;

assembling the trailing hem-forming transverse ribbon around the trailing transverse edge of transversely cut pre-compresses by ultrasonic bonding to form a trailing transverse hem and thereby compresses.

19. The method of continuously manufacturing compresses according to claim 18 further comprising the following steps:

delivering a second strip of hydrophilic cotton gauze from a second gauze supply spool simultaneously with the first strip of hydrophilic cotton gauze and disposed such that the second strip of hydrophilic cotton gauze follows the first non-woven strip;

delivering a second non-woven strip from a second non-woven strip supply spool simultaneously with the first strip of hydrophilic cotton gauze such that the second non-woven strip follows the second strip of hydrophilic cotton gauze;

sequentially interposing and transporting the second strip of hydrophilic cotton gauze and the second non-woven.

20. The method of continuously manufacturing compresses according to claim 18 further comprising the following steps:

making the transversely cut compresses by a plurality of superposed alternating strips of hydrophilic cotton gauze and of non-woven strip, wherein the two strips of hydrophilic cotton gauze are disposed on respective outer sides of the transversely cut compresses;

integrating an X-ray-detectable thread in at least one of the longitudinal hems and transverse hems;

running together the first strip of hydrophilic cotton gauze, the first non-woven strip, and the last strip of hydrophilic cotton gauze to form the multi-layer strip with the first motorized drive device prior to reaching stations for making up individual compresses, wherein the first strip of hydrophilic cotton gauze and the last strip of hydrophilic cotton gauze are disposed on outer sides of the multi-layer strip;

delivering the first continuous non-woven longitudinal band by a first band supply spool;

folding the first continuous non-woven longitudinal band around the first longitudinal edge of the multi-layer strip over the first strip of hydrophilic cotton gauze and the last strip of hydrophilic cotton gauze disposed on the outer sides of the multi-layer strip;

delivering the second continuous non-woven longitudinal band by a second band supply spool;

folding the second continuous non-woven longitudinal band around the second longitudinal edge of the multi-layer strip over the first strip of hydrophilic cotton gauze and the last strip of hydrophilic cotton gauze disposed on the outer sides of the multi-layer strip;

sucking up dust by means of a suction device.

21. The method of continuously manufacturing compresses according to claim 18 further comprising the following steps:

connecting the first strip of hydrophilic cotton gauze to a first gauze device for automatically adjusting a tension of the first strip of hydrophilic cotton gauze;

connecting the first non-woven strip to a first non-woven device for automatically adjusting a tension of the first non-woven strip;

connecting the last strip of hydrophilic cotton gauze to a last gauze device for automatically adjusting the tension of the last strip of hydrophilic cotton gauze.

22. A method of continuously manufacturing compresses or drapes for single use comprising the following steps:

connecting supply reels to a device for automatically adjusting the tension of strips of hydrophilic cotton gauze and of non-woven hydrophilic web;

simultaneously delivering strips of hydrophilic cotton gauze and of non-woven hydrophilic web from the supply reels;

running said strips of hydrophilic cotton gauze and of non-woven hydrophilic web together through a motorized drive device for forming a multilayer strip constituted of a plurality of superposed alternating strips of said hydrophilic cotton gauze and of non-woven hydrophilic web, with outer strips of said multilayer strip being of hydrophilic cotton gauze;

delivering continuous non-woven ribbons or bands from spools;

placing the continuous non-woven ribbons or bands on longitudinal edges of the multilayer strip;

folding the continuous non-woven ribbons or bands around the longitudinal edges of the multilayer strip and over said outer strips to form first hems;

assembling the continuous non-woven ribbons or bands that are folded around the longitudinal edges of the multilayer strip in a stitching station;

generating stitches through said first hems and through all layers of the multilayer strip; cutting the multilayer strip transversely to a longitudinal direction in a cutting station to separate individual compresses or drapes, wherein individual compresses or drapes are made up in stations from the multilayer strip;

taking up the transversely cut compresses or drapes in a direction perpendicular to the longitudinal direction of the multilayer strip by a drive device; and placing hem-forming second ribbons or bands forming second hems around transverse edges of individualized compresses or drapes;

attaching the transverse edges of individualized compresses or drapes to the hem-forming second ribbons or bands by stitching;

finishing the transverse edges by means of said second ribbons or bands that form hems.

23. The method according to claim 22 further comprising producing the hem-forming second ribbons or bands of a non-woven material;

delivering hem-forming second ribbons or bands from second spools;

folding the hem-forming second ribbons or bands around the transverse edges of the individualized compresses or drapes to form second hems.

24. A compress obtained by a method comprising the following steps:

delivering a first strip of hydrophilic cotton gauze from a first gauze supply spool;

delivering a first non-woven strip from a first non-woven strip supply spool simultaneously with the first strip of hydrophilic cotton gauze;

delivering a last strip of hydrophilic cotton gauze from a last gauze supply spool simultaneously with the first strip of hydrophilic cotton gauze;

sequentially superposing and transporting the first strip of hydrophilic cotton gauze, the first non-woven strip and the last strip of hydrophilic cotton gauze in a first motorized drive device and thereby obtaining a single continuous multilayer strip having a first longitudinal edge and having a second longitudinal edge;

folding a first continuous non-woven longitudinal band around the first longitudinal edge;

folding a second continuous non-woven longitudinal band around the second longitudinal edge;

assembling the first continuous non-woven longitudinal band around the first longitudinal edge in a bonding station by means of ultrasonic bonds passing through to form a first hem;

assembling the second continuous non-woven longitudinal band around the second longitudinal edge in the bonding station by means of ultrasonic bonds passing through to form a second hem and thereby a multilayer strip with longitudinally attached hems;

cutting the multilayer strip with longitudinally attached hems to a predefined length in a cutting station with a cut disposed perpendicular to a longitudinal direction to form individual transversely cut pre-compresses having a leading transverse edge and having a trailing transverse edge;

taking up the transversely cut pre-compresses in a perpendicular direction with a second motorized drive device;

folding a leading hem-forming transverse ribbon around the leading transverse edge of transversely cut pre-compresses;

folding a trailing hem-forming transverse ribbon around the trailing transverse edge of transversely cut pre-compresses;

assembling the leading hem-forming transverse ribbon around the leading transverse edge of transversely cut pre-compresses by ultrasonic bonding to form a leading transverse hem;

assembling the trailing hem-forming transverse ribbon around the trailing transverse edge of transversely cut pre-compresses by ultrasonic bonding to form a trailing transverse hem and thereby compresses.

25. A compress for single use comprising a first strip section of hydrophilic cotton gauze;

a first non-woven strip section superposed to the first strip section of hydrophilic cotton gauze;

a last strip section of hydrophilic cotton gauze superposed to the first non-woven strip section, wherein said first strip section of hydrophilic cotton gauze, said non-woven strip section and said last strip section of hydrophilic cotton gauze are superposed and form a multilayer strip section having a first longitudinal edge and having a second longitudinal edge and having a leading transverse edge and having a trailing transverse edge;

a first non-woven longitudinal band section folded around the first longitudinal edge and bonded to the multilayer strip section;

a second non-woven longitudinal band section folded around the second longitudinal edge and bonded to the multilayer strip section;

a leading hem-forming transverse ribbon section folded around the leading transverse edge and bonded to the multilayer section;

a trailing hem-forming transverse ribbon section folded around the trailing transverse edge and bonded to the multilayer section.

* * * * *